United States Patent
Stevens et al.

[11] Patent Number: 5,935,112
[45] Date of Patent: Aug. 10, 1999

[54] HEMOSTASIS VALVE WITH CATHETER/GUIDEWIRE SEALS

[76] Inventors: Brian W. Stevens, 1560 W. 1800 North, Pleasant Grove, Utah 84062; Arlin Dale Nelson, 1465 E. 9200 South, Sandy, Utah 84093

[21] Appl. No.: 08/950,627

[22] Filed: Oct. 15, 1997

[51] Int. Cl.$^6$ .................................................. A61M 5/178
[52] U.S. Cl. .......................... 604/256; 604/246; 604/167
[58] Field of Search ..................................... 604/167, 245, 604/246, 247, 248, 256, 164, 169, 283

[56] References Cited

U.S. PATENT DOCUMENTS

| | | | |
|---|---|---|---|
| 4,723,550 | 2/1988 | Bales et al. | 128/344 |
| 4,857,062 | 8/1989 | Russell | 604/256 |
| 4,978,341 | 12/1990 | Niederhauser | 604/167 |
| 5,009,391 | 4/1991 | Steigerwald | 251/149.1 |
| 5,059,186 | 10/1991 | Yamamoto et al. | 604/280 |
| 5,195,980 | 3/1993 | Catlin | 604/167 |
| 5,269,764 | 12/1993 | Vetter et al. | 604/167 |
| 5,324,271 | 6/1994 | Abiuso et al. | 604/167 |
| 5,338,313 | 8/1994 | Mollenauer et al. | 604/249 |
| 5,338,314 | 8/1994 | Ryan | 604/284 |
| 5,350,364 | 9/1994 | Stephens et al. | 604/167 |
| 5,352,215 | 10/1994 | Thome et al. | 604/284 |
| 5,507,732 | 4/1996 | McClure et al. | 604/280 |
| 5,591,137 | 1/1997 | Stevens | 604/256 |
| 5,599,327 | 2/1997 | Sugahara et al. | 604/283 |
| 5,693,025 | 12/1997 | Stevens | 604/167 |
| 5,700,251 | 12/1997 | Miyauchi et al | 604/264 |

*Primary Examiner*—Corrine McDermott
*Assistant Examiner*—Cris L. Rodriguez

[57] ABSTRACT

A hemostasis valve which includes a tubular body having a lumen therethrough and an elongated housing attached to the tubular body. The body has a recess formed in one end. The housing has a longitudinal bore at one end and a compression chamber formed at another end which communicates with the bore. A resilient seal which comprises a cone-shaped membrane portion disposed in the recess for substantially blocking and controlling the loss of body fluids from the lumen. A compressible second seal for selectively opening and closing the bore in response to a compressive force is disposed in the compression chamber. The compressible seal has a longitudinal first passageway that communicates with the bore and a raised annular portion which serves as a selective opening to the bore. The compressible seal responds to compressive forces so as to reduce or increase the size of the opening provided by the raised annular portion to selectively seal or unseal the bore. The hemostasis valve includes a rotatable end cap configured to exert a compressive force on the compressible seal when rotated in one direction relative to the housing, and releases the compressive force when rotated in an opposite direction. The compressible seal is configured to allow an instrument accessing the lumen to be repositioned or removed while maintaining an adequate seal capable of preventing substantially all loss of the body fluids beyond the compressible seal without the user having to rotate the end cap to release the compressive force acting on the compressible seal.

26 Claims, 10 Drawing Sheets

HEMOSTASIS VALVE WITH CATHETER/GUIDEWIRE SEALS

BACKGROUND OF THE INVENTION

1. The Field of the Invention

The present invention relates to valves, and, in particular, relates to hemostasis valves.

2. Relevant Technology

Several current surgical procedures require temporary and often repeated introduction and removal of catheters and/or guidewires within the cardiovascular system of a patient. For example, using only a relatively small incision, a catheter can be introduced into the body of a patient and used to deliver a fluid, such as a medication, directly to a predetermined location within the cardiovascular system. Catheters can also be used for exploratory surgery and for removing tissue samples within a patient's body. One increasingly common use for catheters is in the placement of small balloons that can be selectively inflated within a blood vessel. The balloons are used for opening blood vessels that have been blocked or partially blocked by fat build-up. This opening or altering of the vein is referred to as angioplasty.

A common catheter design used in performing many of the procedures includes an elongated, flexible, cylindrical catheter body having a fluid flow passageway or a lumen extending along the interior of that catheter body. During one type of use, an end of the catheter is inserted into the body of the patient through an incision in a blood vessel in the cardiovascular system. The catheter is advanced along the internal passageway of the vessel until the end of the catheter is located at a desired predetermined location for conducting an intended activity.

A guidewire is a long, cylindrical, flexible wire that is commonly used for directing the catheter to the desired location within the body. A guidewire is typically smaller in diameter and more rigid than a catheter. It is, therefore, easier for a surgeon to first direct and advance a guidewire within the cardiovascular system to the desired location within the body of the patient. The opposing end of the guidewire, positioned outside the body of the patient, is then received within the lumen of the catheter. Using the guidewire as a guide, the catheter is advanced along the length of the guidewire so as to properly position the catheter within the body of the patient. If desired the guidewire can then be removed from within the catheter to open the lumen of the catheter. In an alternative process for inserting the catheter, the guidewire is initially received within the lumen of the catheter and the catheter and guidewire are simultaneously advanced within the cardiovascular system of the patient.

Operations using catheters can often require the insertion and removal of several different types of catheters and guidewires. One of the problems encountered with the insertion and removal of catheters and guidewires is controlling bleeding at the point where the catheters and guidewires are first introduced into the cardiovascular system.

In one approach to controlling bleeding and ensuring easy insertion and removal of the catheter and/or guidewire within the cardiovascular system, one end of an introducer is first secured within a large vein of a patient. An introducer is a relatively large, hollow tube. The opposite end of the introducer is positioned outside the body of the patient and is attached to an adapter.

An adapter typically comprises a short, rigid tube having a passageway extending therethrough. Attached at one end of the adapter tube is a connector. The connector is used to connect the passageway of the adapter to the exposed end of the introducer. This enables fluids and/or medical instruments, such as catheters and guidewires, to pass between the adaptor and the introducer.

Positioned at the opposite end of the adaptor tube, is a valve commonly referred to as a hemostasis valve. The hemostasis valve includes an enlarged chamber portion at the end of the adaptor remote from the patient. The chamber is aligned with and is connected to the passageway extending through the adaptor.

Positioned within the chamber is some type of seal. The adaptor may have more than one seal disposed therein. During use of the adaptor, the pressure of the blood of the patient caused by the beating of their heart can cause blood from the patient to flow up through the introducer and into the passageway of the adaptor tube. The one or more seals, which either independently close or are compressed around the catheter or guidewire, prevent blood from escaping out of the adaptor through the access of the valve.

Various seal arrangements are available with different types of hemostasis valves ranging from one seal to a plurality of seals. One of the main purposes of the valve arrangement is to be able to block off the passage way to prevent the loss of bodily fluids through the hemostasis valve. One type of seal that has been used in hemostasis valves is a soft, cylindrical, compressible seal. The compressible seal has a passageway extending along the length of the seal. The seal is oriented in the chamber so that the passageway through the seal is aligned with and connected to the passage in the adaptor tube.

To seal a hemostasis valve incorporating a compressible seal around an inserted catheter or guidewire, a portion of the hemostasis valve is advanced, which in turn compresses the seal within the chamber, causing the passageway in the compressible seal to constrict. If the shaft is advanced sufficiently far within the chamber, the passageway in the seal constricts so as to form a seal around the exterior surface of the catheter or guidewire positioned in the passageway. Alternatively, if the catheter or guidewire is removed from within the seal, the passageway in the seal can constrict in response to compressive force so that the seal completely closes off the access through the valve.

When a single compressible seal is used, there tends to be a loss of bodily fluid from the patient, especially when the catheter or guidewire is removed. A single seal is more prone to resulting in needless blood loss and increases the risk of contamination of the blood of the patient. Furthermore, the leakage of bodily fluids such as blood may produce a messy and slippery work environment for the surgeon. With the increasing number of blood transmitted diseases, such as AIDS, blood leakage from the adaptor greatly increases the risk to the surgeon and other medical personnel.

Attempts have been made to solve the leakage problem by making hemostasis valves that utilize two or more seals. Typical seals include duck-bill valves and slit valves. While multiple seals in the hemostasis valve are useful in helping to reduce the loss of body fluids, including blood, several problems still exist. Current hemostasis valves, regardless of whether the valve has one or two seals, generally have an open position and a closed or sealed position. Once the hemostasis valve has been closed, the surgeon is not able to move or reposition the catheter or guidewire without putting the hemostasis valve into the open position; however, this can permit body fluids to escape through the valve. For example, if the valve utilizes a compressible seal, the catheter or guidewire cannot be repositioned or removed unless substantially all of the compressive force is removed from the compressible seal. Once the compressive force is removed, the hemostasis valve is no longer able to properly seal. Thus, conventional hemostasis valves are unable to provide a seal against the loss of bodily fluids while still allowing the catheter or guidewire within the valve to be repositioned.

An additional problem with existing hemostasis valves is that the seals, and in particular those seals that are compressed to form a seal, tend to exert a force upon the catheter or guidewire. The forces, including the frictional forces acting on the instrument, are commonly referred to as "drag". The drag acting on the catheter or guidewire disposed in a seal makes it difficult for the surgeon to be able to adjust the catheter or guidewire. In particular, the drag reduces the ability to adjust the catheter or guidewire by the "feel" of the movement. Conventional hemostasis valves must be adjusted to remove the compressive forces acting on the seal. However, removing the compressive forces acting on the seal can result in fluid leakage as discussed above.

Finally, having to first remove the compressive force, then reposition or remove the catheter or guidewire, and finally readjust the hemostasis valve to compress the seal so as to form a seal is time consuming and in turn unnecessarily lengthens the procedure.

It will be desirable to have a hemostasis valve that includes one or more seals that is able to accommodate both large and small diameter catheters and guidewires, is able to minimize blood leakage from the hemostasis valve and remain sealed while allowing the catheter or guidewire to be repositioned without the loss of bodily fluids or blood. It would also be advantageous to have a hemostasis valve in which the seal will remain sealed but which will allow an instrument such as a catheter or guidewire to be longitudinally repositioned without exerting so much drag on the catheter or the guidewire that the surgeon is unable to have a feel for the movement of the guidewire or catheter.

Such improved hemostasis are disclosed and claimed herein.

SUMMARY AND OBJECTS OF THE INVENTION

It is, therefore, an object of the present invention to provide an improved hemostasis valve which minimizes the loss of body fluids during repositioning or removing of medical instruments, such as catheters and guidewires, from the hemostasis valve.

It is another object of the present invention to provide an improved hemostasis valve that is capable of being sealed to prevent the loss of body fluids while still allowing longitudinal movement of the catheter or guidewire through the hemostasis valve.

It is yet another object of the present invention to provide an improved hemostasis valve that includes a compression seal which allows the hemostasis valve to be sealed while still allowing the catheter or guidewire be longitudinally repositioned without having to completely remove the compressive forces acting on the seal.

It is a further object of the present invention to provide an improved hemostasis valve in which the forces acting on the catheter or guidewire while the catheter or guidewire is being repositioned can be selectively reduced while maintaining the seal.

Still another object of the present invention is to provide an improved hemostasis valve that allows the repositioning or removal of the catheter or guidewire with increased speed and substantially without the loss of body fluids.

Yet another object is to provide an improved hemostasis valve which incorporates a compression seal but enables a surgeon to move or reposition a catheter or seal by "feel" while still maintaining a sealed configuration in the valve.

These and other objects and features of the present invention will become more fully apparent in the following description and appended claims, or may be learned by the practice of the invention as is set forth herein.

To achieve the foregoing objects, in accordance with the invention as embodied and broadly described herein, a hemostasis valve is provided that has a resilient seal and a compressible seal. The resilient seal substantially stops the flow of fluids from the lumen and the compressible seal stops any fluid that passes beyond the resilient seal. When compressive force is exerted on the compressible seal, a portion of the compressible seal moves radially inward to form a progressively tighter seal. This is particularly important when an elongated instrument, such as a catheter or a guidewire, is disposed in the lumen. The amount of compressive force that is being exerted on the compressible seal can be incrementally adjusted so that a seal is formed or maintained around the elongated instrument while still allowing the instrument to be repositioned or even removed without having to remove substantially all of the compressive force acting on the compressible seal.

A hemostasis valve is provided that includes an elongated tubular body having a lumen therethrough and which is adapted for accessing the cardiovascular or other intravenous system of a patient. An interior recess is located at a proximal end of the tubular body which is in communication with the lumen. Preferred hemostasis valves also include an elongated housing with a longitudinal bore formed therethrough that is attached to the proximal end of the tubular body. The housing has an interior hollow compression chamber formed in a proximal end thereof that is in communication with the bore.

The hemostasis valve further comprises a resilient seal and a resiliently deformable compressible seal. The resilient seal substantially blocks and controls the loss of body fluids from the tubular body. The resilient seal comprises a generally cone-shaped membrane portion having an aperture formed through the apex thereof.

The compressible seal selectively opens and closes the longitudinal bore in the housing in response to a compressive force exerted on the compressible seal. The compressible seal is elongated and has a longitudinal passageway therethrough that serves as an opening to the lumen of the tubular body. The compressible seal preferably includes a raised annular portion formed in the longitudinal passageway. The compressible seal generally assumes a normally open position when not subjected to a compressive force, but responds to compressive forces by a portion of the compressible seal moving radially inward so as to progressively reduce the size of the opening provided by first longitudinal passageway until the compressible seal is completely closed if desired.

The hemostasis valves of the present invention also include an end cap that selectively increases the compressive force on the compressible seal when the end cap is rotated in one direction relative to the elongated housing and selectively decreases the compressive force acting on the compressible seal when rotated in an opposite direction relative to the elongated housing.

The compressible seal is configured to allow an instrument accessing the lumen in the tubular body to be moved or replaced even though the compressible seal is able to maintain a seal capable of preventing substantially all loss of the body fluids beyond the compressible seal without rotating the end cap to release substantially all of the compressive force acting on the compressible seal.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention is an improved hemostasis valve with a valve assembly that minimizes the loss of body fluids during repositioning or removing of medical instruments, such as catheters and guidewires, from the hemostasis valve. The improved valve assembly includes a compressible seal that allows the hemostasis valve to remain sealed while still allowing the catheter or guidewire to be longitudinally repositioned or removed without having to remove substantially all the compressive forces acting on the compressive seal.

The inventive hemostasis valve includes a resilient seal and a compressible seal. The resilient seal substantially stops the flow of fluids out of the hemostasis valve and the compressible seal stops any fluid that passes beyond the resilient seal. The compressible seal responds to compressive forces exerted thereon to seal the hemostasis valve. When compressive force is exerted on the compressible seal, a portion of the compressible seal moves radially inward to form a progressively tighter seal around a catheter or guidewire that is disposed in the compressive seal. The amount of compressive force that is being exerted on the compressible seal can be incrementally adjusted so that a seal is formed or maintained around the catheter or guidewire while still allowing the catheter or guidewire to be repositioned or even removed without having to remove substantially all of the compressive force acting on the compressible seal.

Figure 1:
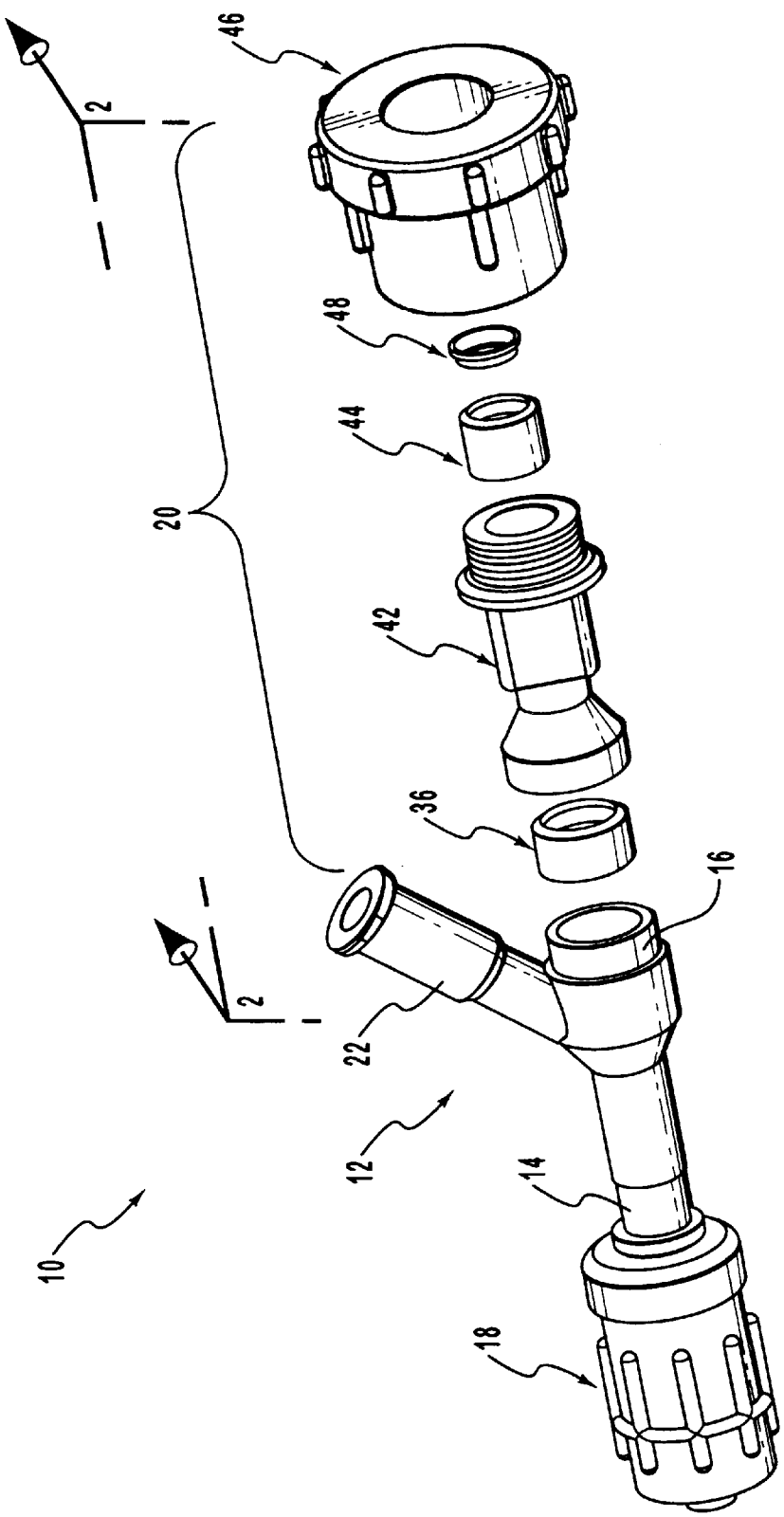
FIG. 1 is an enlarged prospective view of an adaptor having a rotatable end cap and a valve assembly in a partially disassembled condition.

FIG. 1 depicts an adaptor 10 comprising a tubular body 12, a rotatable connector 18, and a valve assembly 20. Tubular body 12 has a distal end 14 and an opposing proximal end 16. Rotatable connector 18 is positioned at distal end 14 of tubular body 12. Rotatable connector 18 provides fluid coupling between an introducer (not shown) and tubular body 12. Valve assembly 20 is positioned at proximal end 16 of tubular body 12.

One embodiment of tubular body 12 includes a first supplemental access tube 22 attached thereto. First supplemental access tube 22 has a central bore formed therethrough so as to be in fluid communication with tubular body 12. In addition, first supplemental access tube 22 is configured to be placed in fluid communication with an elongated device. such as a catheter. First supplemental access tube 22 can be used to introduce fluids or medical devices into the body of a patient. It can be appreciated that tubular body 12 may have various other configurations in order to carry out an intended function.

First supplemental access tube 22 is preferably positioned at an angle relative to the longitudinal axis of tubular body 12 so as to project outwardly from tubular body 12 towards proximal end 16. As shown in FIG. 1, the remote end of first supplemental access tube 22 has threads formed thereon to accommodate a conventional Luer lock attachment. Various other types of attachment structure may perform the attaching function thereof equally effectively.

Valve assembly 20 preferably includes a resilient seal 36, a compressible seal 44, and a rotatable end cap 46. Valve assembly 10 also includes an elongated housing 42 and a slip ring 48. The configuration and interrelationships of these components are more clearly shown in FIG. 2, which depicts a partial cross-sectional exploded view of valve assembly 20. Tubular body 12 has a longitudinal passageway or lumen 50 extending through tubular body 12. At proximal end 16, tubular body 12 has an interior recess 52 that is axially aligned with lumen 50. Interior recess 52 has a proximal end 54 and a distal end 56. The diameter of interior recess 52 is defined by an interior surface 60 that extends between proximal end 54 and distal end 56 of interior recess 52.

Lumen 50 communicates at proximal end 58 thereof with distal end 56 of interior recess 52. Lumen 50 is concentric with interior recess 52 and has an interior surface 59 with a diameter smaller than the diameter formed by interior surface 60 of interior recess 52. Lumen 50 and interior recess 52 are preferably substantially cylindrical.

A first annular shoulder 64 projects proximally from proximal end 58 of lumen 50 into distal end 56 of interior recess 52. First annular shoulder 64 adjacently encircles lumen 50 and has an outer diameter smaller than the diameter of interior surface 60 of interior recess 52. A first annular receiving groove 66 is formed between first annular shoulder 64 and interior surface 60. First annular retaining groove 66 is configured to receive resilient seal 36 therein.

Tubular body 12 has an exterior surface 13 that is substantially cylindrical-shaped. Tubular body 12 is one embodiment of a structure capable of performing the function of a body means for providing lumen 50 therethrough and which is adapted for accessing the cardiovascular or other intravenous system of a patient. It can be appreciated that various other embodiments of a body means may be equally effective in carrying out the intended function thereof.

Resilient seal 36 is configured to cooperate with first annular receiving groove 66 in interior recess 52 of tubular body 12. Resilient seal 36 comprises a substantially cylindrical body portion 38 having an exterior surface 68 and an interior surface 70 extending between a proximal end 72 and a distal end 74. Interior surface 70 defines an inner diameter of body portion 38. Exterior surface 68 of body portion 38 has an outer diameter approximately equal to the diameter formed by interior surface 60 of interior recess 52 such that resilient seal 36 can be received within interior recess 52. Distal end 74 of resilient seal 36 is received within first annular receiving groove 66. First annular shoulder 64 in interior recess 52 of tubular body 12 is configured to retain distal end 74 of resilient seal 36 in first annular retaining groove 66.

Figure 2:
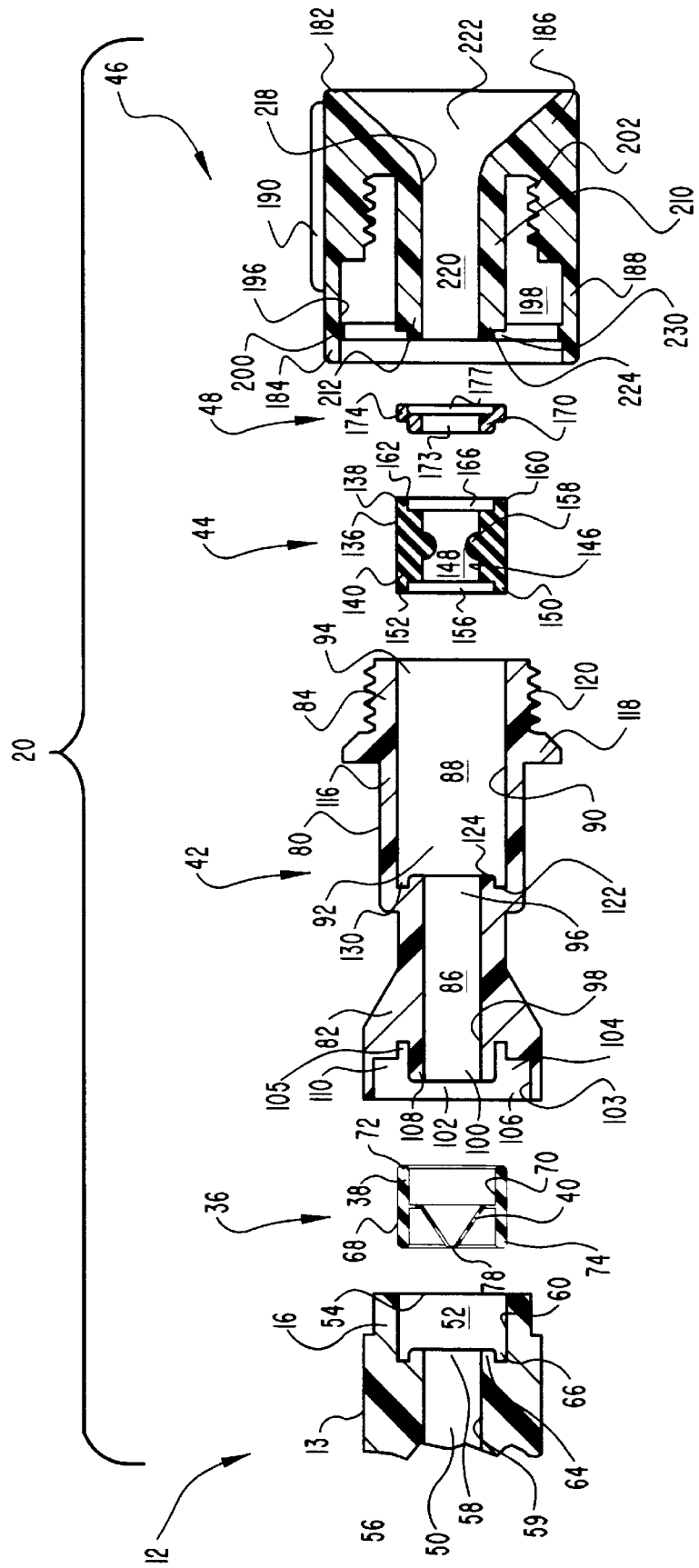
FIG. 2 is an enlarged cross-sectional view of a portion of the valve assembly of FIG. 1 in a partially disassembled condition.

Various other configurations of first annular retaining groove 66 and distal end 74 of resilient seal 36 may be equally effective in carrying out the intended function thereof. As depicted in FIG. 2, distal end 74 and first annular retaining groove 66 are shown as being substantially rectangular-shaped. They could, however have various other shapes. What is important is that distal end 74 be configured to cooperate with first annular retaining groove 66 sufficiently to form a seal between proximal end 16 of tubular body 12 and distal end 74 of resilient seal 36 and to hold resilient seal 36 in place within interior recess 52.

Figure 5:
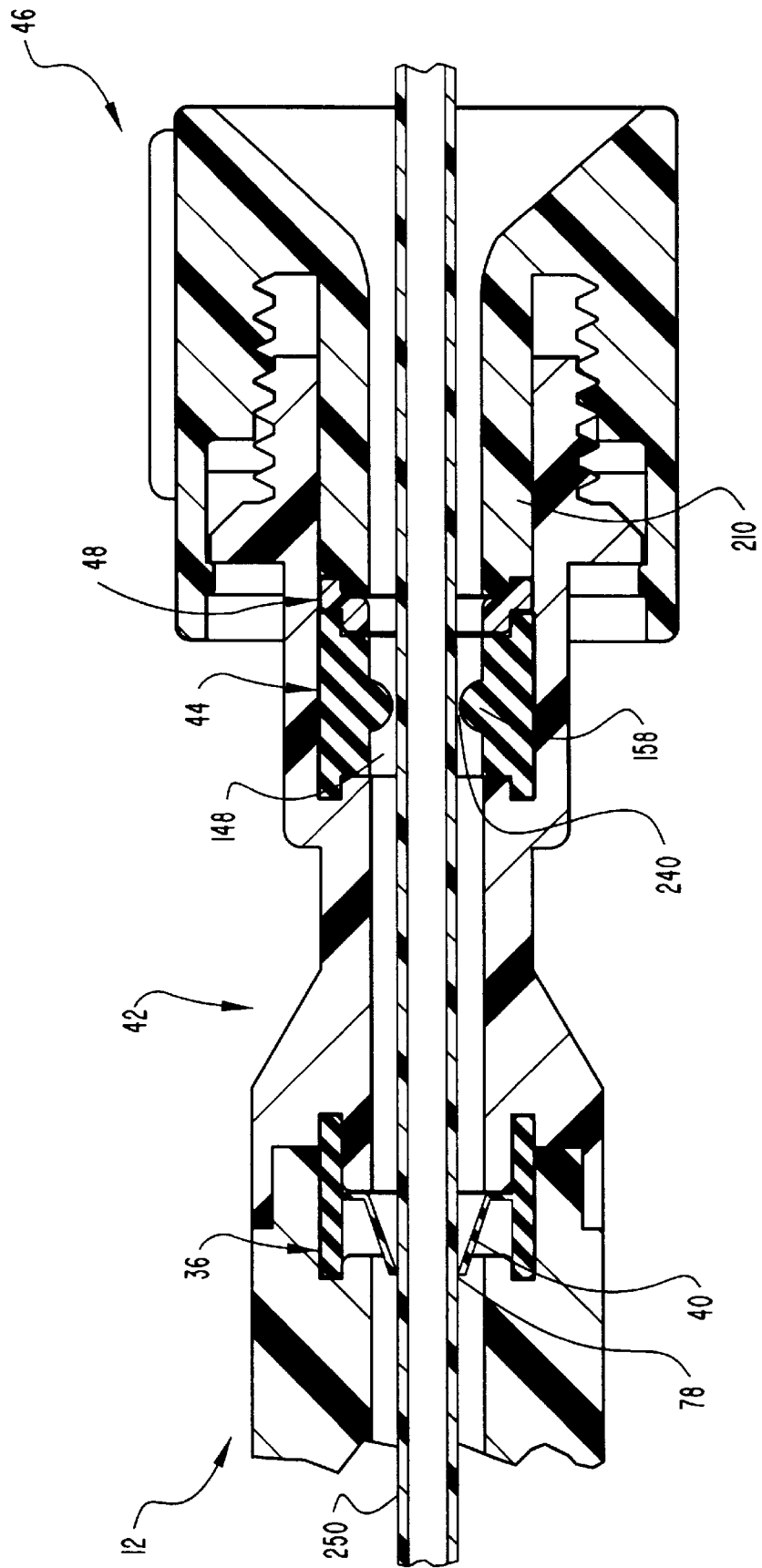
FIG. 5 is an enlarged cross-sectional view of the valve assembly of Figure 3 with an elongated instrument therethrough.

Resilient seal 36 also comprises a resilient membrane 40 that is attached to interior surface 70 of body portion 38. Resilient membrane 40 extends across the inner diameter of body portion 38. Membrane 40 is thin and relatively flexible. Membrane 40 has an aperture 78 formed therethrough. In one embodiment of resilient seal 36 illustrated in FIG. 2, membrane 40 is cone-shaped. Membrane 40 may have other configurations such as being semi-spherical shaped, flat, or elliptical while substantially providing the intended function thereof. In a preferred embodiment, cone-shaped membrane 40 has aperture 78 formed at the apex thereof. Aperture 78 is axially aligned with lumen 50. An elongated instrument 250, such as by way of example and not limitation, a catheter or guidewire, can be disposed through aperture 78 as depicted in FIG. 5.

When resilient seal 36 is disposed in first annular retaining groove 66 in interior recess 52, cone-shaped membrane 40 is capable of substantially blocking the loss of body fluids from lumen 50 and substantial sealing around any elongated instrument 250 residing within adaptor 10. Resilient seal 36 preferably is substantially composed of silicon rubber, but may comprise other elastomer compatible materials. Resilient seal 36 is one embodiment of structure capable of performing the function of a resilient first sealing means for substantially blocking and controlling the loss of body fluids from lumen 50.

Valve assembly 20 further comprises elongated housing 42 that has a longitudinal bore 86. As shown in FIG. 2, housing 42 has an exterior surface 80, a distal end 82, and a proximal end 84. Distal end 82 of housing 42 has an opening 102 formed therein that is in communication with bore 86 and is configured to receive both proximal end 72 of resilient seal 36 and proximal end 16 of body 12 therein. Opening 102 has a proximal end 104 and a distal end 106. An inner surface 103 of opening 102 has a diameter approximately equal to the diameter of outside surface 13 of proximal end 16 of body 12. Bore 86 communicates at a distal end 100 thereof with proximal end 104 of opening 102. Bore 86 is concentric with opening 102 and has an interior surface 98 that has a diameter smaller than the diameter of opening 102 formed by inner surface 103. Opening 102 is preferably cylindrical.

A second annular shoulder 108 is formed at proximal end 104 of opening 102 and extends distally into opening 102. Second annular shoulder 108 and inner surface103 define a first annular recess 110 that is configured to receive proximal end 16 of tubular body 12 and a second annular retaining groove 105 configured to receive proximal end 72 of resilient seal 36. Second annular shoulder 108 encircles bore 86 and assists in defining the diameter thereof. The outside diameter of second annular shoulder 108 is substantially the same as the diameter of interior surface 70 of cylindrical body portion 38 of resilient seal 36. Proximal end 16 of tubular body 12 and distal end 82 of housing 42 enclose resilient seal 36 when valve assembly 20 is in an assembled configuration.

Proximal end 84 of housing 42 has an interior compression chamber 88 that is in communication with bore 86. Compression chamber 88 has an interior diameter defined by an interior surface 90 which extends between a distal end 92 and a proximal end 94 thereof. Bore 86 communicates at a proximal end 96 thereof with distal end 92 of compression chamber 88. Bore 86 is concentric with compression chamber 88 and has a diameter formed by interior surface 98 that is smaller than the inner diameter of compression chamber 88 formed by interior surface 90. Bore 86 and compression chamber 88 are preferably substantially cylindrical.

An end wall 122 extends between proximal end 96 of bore 86 and distal end 92 of compression chamber 88. A first annular ridge 124 projects proximally from end wall 122 and adjacently encircles bore 86. First annular ridge 124 has an outer diameter smaller than the inner diameter formed by interior surface 90 of compression chamber 88. As such, a third annular retaining groove 130 is formed between first annular ridge 124 and interior surface 90 of compression chamber 88. Third annular retaining groove 130 is configured to receive compressible seal 44 therein.

Exterior surface 80 of housing 42 includes a substantially rectangular casing 116 surrounding compression chamber 88. Rectangular casing 116 is configured to provide flat surfaces that enable medical personnel to clamp or use other mechanical means for holding adaptor 10. It can be appreciated that rectangular casing 116 may have alternative embodiments including octagonal or circular cross-sectional configurations that may be equally effective in performing the intended function thereof.

As illustrated in FIG. 2, proximal end 84 of housing 42 has a compression collar 118 extending radially outward from exterior surface 80. Positioned proximal of compression collar 1l18 and encircling proximal end 84 of housing 42 on exterior surface 80 may be first engagement threads 120 which will be discussed later in greater detail.

Housing 42 is one embodiment of structure capable of performing the function of a housing means for providing a longitudinal bore 86 therethrough in communication with lumen 50. It can be appreciated that various other embodiments of structure capable of performing the function of such housing means may be equally effective in carrying out the intended function thereof.

Valve assembly 20 also comprises a resiliently deformable compressible seal 44. Compressible seal 44 is configured to cooperate with third annular retaining groove 130 in compression chamber 88. Compressible seal 44 has an exterior surface 136 extending between a proximal end 138 and a distal end 140. Exterior surface 136 of compressible seal 44 has an outer diameter approximately equal to the diameter of inner surface 90 of compression chamber 88 such that compressible seal 44 can be received within compression chamber 88. In one embodiment of compressible seal 44, depicted in FIGS. 1 and 2, exterior surface 136 has a generally tubular shape. It can be appreciated that exterior surface 136 of compressible seal 44 may have other configurations as long as both compressible seal 44 and compression chamber 88 are configured to cooperate.

Compressible seal 44 has an interior surface 146 that defines a first passageway 148 therein which extends longitudinally through compressible seal 44 and is axially aligned with bore 86. A raised annular portion, such as by way of example and not limitation, raised annular rib 158, is integrally formed on interior surface 146. As depicted in FIG. 2, raised annular rib 158 is semi-spherical in shape. It can be appreciated that the raised annular portion, such as raised annular rib 158, may have various other configurations and perform the functions thereof equally effectively. By way of example and not limitation, raised annular rib 158 may be shaped as half an ellipse, semi-circular, rectangular, half an octagon, or various other shapes. The function and importance of raised annular rib 158 will be discussed in further detail below.

An annular first tongue 150 projects distally from distal end 140 of compressible seal 44. First tongue 150 has a distal end face 152. The inside diameter of first tongue 150 defines a first recess 156 in distal end 140 of compressible seal 44 that is concentric with first passageway 148 and has an inner diameter greater than the interior diameter of first passageway 148 formed by interior surface 146.

An annular second tongue 160 projects proximally from proximal end 138 of compressible seal 44. Second tongue 160 has a proximal end face 162. The inside diameter of second tongue 160 defines a second recess 166 concentric with first passageway 148 of compressible seal 44 that has a diameter greater than the diameter of first passageway 148 formed by interior surface 146. Annular first and second tongues 150 and 160, respectively, encircle the respective ends of first passageway 148.

Compressible seal 44 is one embodiment of structure capable of performing the function of a second sealing means for selectively sealing and unsealing bore 86 in response to a compressive force exerted on second sealing means. Second sealing means has a raised annular portion formed therein configured to allow an elongated instrument 250 accessing lumen 50 through passageway 148 to be repositioned or removed while still maintaining a seal capable of preventing substantially all loss of body fluids beyond the second sealing means without releasing substantially all of the compressive force acting on the second sealing means (FIG. 5). Other embodiments including alternative structures capable of performing the function of such a second sealing means may be equally effective in carrying out the intended function thereof.

First tongue 150 is configured to cooperate with third annular retaining groove 130 and first annular ridge 124 in compression chamber 88. First tongue 150 of compressible seal 44 is received within third annular retaining groove 130 with distal end face 152 of first tongue 150 against annular end wall 122. First annular ridge 124 is received within first recess 156 in distal end 140 of compressible seal 44. As depicted in FIG. 2, first tongue 150, third annular retaining groove 130, and first annular ridge 124 are shown as having a rectangular-shaped cross section.

Various other configurations of first tongue 150, third annular retaining groove 130, and first annular ridge 124 may be equally effective in carrying out the intended function thereof. What is important is that first tongue 150 of compressible seal 44 be configured to cooperate with third annular retaining groove 130 sufficiently to form a seal between distal end 92 of compression chamber 88 and distal end 140 of compressible seal 44 and to evenly compress compressible seal 44 when compressive force is applied thereto. Annular ridge 124 is preferably able to hold distal end 140 of compressible seal 44 in place in distal end 92 of compression chamber 88 and to prevent distal end 140 of compressible seal 44 from slipping into bore 86 when compressible seal 44 is compressed.

First tongue 150, third annular retaining groove 130, and first annular ridge 124 are one example of structure capable of performing the function of a first holding means for interlocking distal end 140 of compressible seal 44 within distal end 92 of compression chamber 88 such that when compressive force is exerted on compressible seal 44, distal end 140 of compressible seal 44 remains firmly in place within housing 42. Various other embodiments of structure capable of performing the function of such a first holding means may be equally effective in carrying out the intended function thereof.

Compressible seal 44 preferably comprises a deformable, resilient material which allows compressible seal 44 to compress in response to a compressive force and either form a seal with itself or form a seal around an elongated instrument 250 positioned through first passageway 148 (FIG. 5). The material comprising compressible seal 44 should also be sufficiently resilient to enable compressible seal 44 to independently conform back to its original configuration when the compressive force is removed. The preferred material for tubular compressible seal 44 is silicon rubber. It is, however, contemplated that compressible seal 44 may be substantially composed of other kinds of conventional rubbers and elastomeric materials.

As depicted in FIGS. 1 and 2, valve assembly 20 includes an optional slip ring 48. Slip ring 48 comprises a first ring 170 having an outer diameter that is substantially the same as the diameter of second recess 166 in proximal end 138 of compressible seal 44. The inner diameter of first ring 170 defines a first access 173. First access 173 is axially aligned with first passageway 148 in compressible seal 44. Proximally attached to first ring 170 is an annular second ring 174. Second ring 174 has an outer diameter greater than the outer diameter of first ring 170 and an inner diameter that defines a second access 177. The diameter of second access 177 is greater than the diameter of first access 173. Second access 177 is concentric with first access 173 and communicates therewith.

First ring 170 is configured to be received within second recess 166 in proximal end 138 of compressible seal 44. Second tongue 160 of compressible seal 44 encircles first ring 170 of slip ring 48 with proximal end face 162 contacting second ring 174 of slip ring 48. As illustrated in FIG. 2, second tongue 160 and first ring 170 are shown as having a substantially rectangular-shaped cross-section. Various other configurations of second tongue 160 and first ring 170 may be equally effective in carrying out the intended function thereof. What is important is that second tongue 160 be configured to cooperate with first ring 170 sufficiently to form a seal between proximal end 138 of compressible seal 44 and slip ring 48. In addition, second tongue 160 and first ring 170 must cooperate sufficiently so that compressive force can be uniformly exerted upon compressible seal 44 without compressible seal 44 twisting out of position. The function of slip ring 48 will be discussed in greater detail below.

Second annular tongue 160 of compressible seal 44, first ring 170 of slip ring 48, and second ring 174 of slip ring 48 are one example of structure capable of performing the function of a second holding means for interlocking proximal end 138 of compressible seal 44 such that when compressive force is exerted on compressible seal 44, proximal end 138 of compressible seal 44 remains firmly in place. Various embodiments of structure capable of performing the function of such a second holding means may be equally effective in carrying out the intended function thereof.

Slip ring 48 is one embodiment of structure capable of performing the function of a ring means for a rotatable connection to the second sealing means so as to reduce rotation and twisting of the second sealing means when compressive forces are exerted on the second sealing means. Various other embodiments of structure capable of performing the function of such a ring means may be equally effective.

Rotatable end cap 46, shown in FIG. 2, is substantially cylindrical and has a proximal end 182 and an opposing distal end 184. End cap 46 comprises an end wall 186 on proximal end 182 thereof and a side wall 188 integrally formed with end wall 186. A plurality of gripping ribs 190 extend radially outward on the periphery of end cap 46 and are aligned with the longitudinal axis of body 12 and housing 42. End cap 46 has an outer diameter greater than housing 42.

Sidewall 188 has an interior surface 196 that defines a recessed chamber 198 in distal end 184 of end cap 46. A compression ring 200 extends radially inward from interior surface 196 of side wall 188 and has an inner diameter slightly smaller than the outer diameter of compression collar 118 on proximal end 84 of housing 42. Positioned proximal to compression ring 200 are second engagement threads 202. Second engagement threads 202 are configured for rotational, threaded engagement with first engagement threads 120 on proximal end 84 of housing 42.

Rotatable end cap 46 further comprises a tubular shaft 210 that projects distally from end wall 186 within recessed chamber 198. Shaft 210 has a distal end 212. Shaft 210 also has an interior surface 218 that defines an entryway 220. Entryway 220 extends longitudinally through shaft 210 and end wall 186. Interior surface 218 of entryway 220 expands radially outward at proximal end 182 of end cap 46 to form an enlarged retaining mouth 222.

A second annular ridge 224 projects distally from distal end 212 of shaft 210 and encircles entry way 220 that extends through shaft 210. Second annular ridge 224 has an outer diameter that is substantially the same as the inner diameter of second ring 174 of slip ring 46. The outer diameter of second annular ridge 224 is smaller than the outer diameter of shaft 210 so as to define a fourth annular retaining groove 230 when shaft 210 is received within compression chamber 88 Fourth annular retaining groove 230 is configured to receive either second ring 174 or second tongue 160 on proximal end 138 of compressible seal 44 therein, depending on whether the embodiment of valve assembly 20 includes optional slip ring 48.

Rotatable end cap 46 is one example of structure capable of performing the function of a compressing means for exerting compressive force on the second sealing means when the compressing means is rotated in one direction relative to the housing means and for releasing compressive force from the second sealing means when rotated in the opposite direction relative to the housing means. Various embodiments of structure capable of performing the function of such a compressing means are equally effective in carrying out the intended function thereof.

Figure 3:
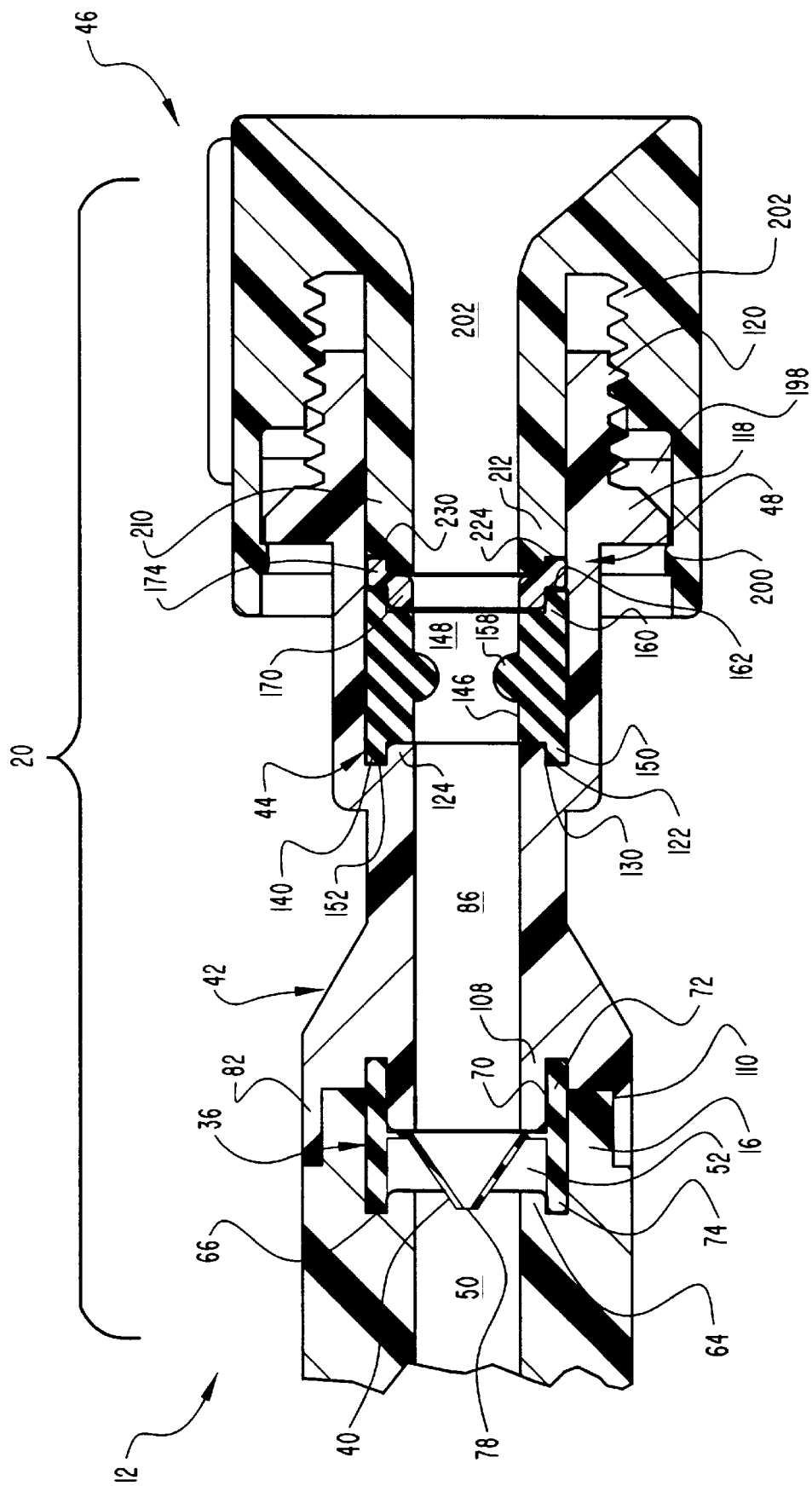
FIG. 3 is an enlarged cross-sectional view of a portion of the valve assembly of FIG. 1 in an assembled condition showing a compressible seal in an uncompressed position.

FIG. 3 illustrates an assembled valve assembly 20 prior to any compressive force being exerted on compressible seal 44. Distal end 74 of resilient seal 36 is disposed within tubular body 12. First annular shoulder 64 is shown holding distal end 74 of resilient seal 36 in place within interior recess 52 and prevents distal end 74 from sliding into lumen 50, although cone-shaped resilient membrane 40 may partially extend into lumen 50. Cone-shaped membrane 40 is configured to substantially block and control the loss of fluids from lumen 50 to bore 86.

Referring to FIGS. 2 and 3, distal end 82 of housing 42 encloses proximal end 72 of resilient seal 36 and proximal end 16 of body 12. Second annular shoulder 108 contacts interior surface 70 of proximal end 72 of resilient seal 36. Second annular shoulder 108 prevents proximal end 72 of resilient seal 36 from moving out of position into opening 102.

Housing 42 may be attached to tubular body 12 using a conventional adhesive, although other methods of connecting housing 42 to proximal end 16 of tubular body 12 may be equally effective in carrying out the intended function thereof. By way of example and not limitation, distal end 82 of housing 42 may also be connected to proximal end 16 of tubular body 12 by an interference fit or a snap fit.

Compressible seal 44 is disposed into compression chamber 88 in proximal end 84 of housing 42. First tongue 150 on distal end 140 of compressible seal 44 is disposed in third annular retaining groove 130 (FIG. 2) in distal end 92 of compression chamber 88. First annular ridge 124 is disposed in first recess 156 (FIG. 2) of compressible seal 44. First annular ridge 124 prevents compressible seal 44 from moving out of position and blocking bore 86 of housing 42 as compressible seal 44 is being compressed. Distal end face 152 of first tongue 150 contacts annular end wall 122.

The embodiment depicted in FIG. 3 incldes slip ring 48 disposed in compression chamber 88 against second tongue 160 of compressible seal 44. First ring 170 of slip ring 48 is disposed in second recess 166 (FIG. 2) of compressible seal 44 and prevents second tongue 160 from moving out of position as compressible seal 44 is compressed. Annular proximal end face 162 of second tongue 160 of compressible seal 44 contacts and seals with second ring 174 of slip ring 48.

The function of slip ring 48 is to prevent twisting of compressible seal 44 as shaft 210 is advanced within compression chamber 88. As shaft 210 is advanced while rotating as part of end cap 46, distal end 212 of shaft 210 pushes against slip ring 48 instead of seal 44. Since slip ring 48 comprises a material that allows it to slip relative to shaft 210, this reduces the tendency of shaft 210 to cause compressible seal 44 to twist. Substantial twisting of compressible seal 44 could cause compressible seal 44 to apply a counter rotating force to shaft 210 which, if sufficient, could independently back-off or unscrew shaft 210 from within compression chamber 88, thereby undesirably opening compressible seal 44 and possibly causing unintended fluid leakage.

To facilitate slippage between shaft 210 and slip ring 48, slip ring 48 is preferably made of a relatively rigid material having a relatively low coefficient of friction, such as polytetrafluorethylene, or more commonly known as Teflon®. To assist in rotational slipping between shaft 210 and slip ring 48 and to provide a smoother interaction between the components within valve assembly 20, a small quantity of oil or other lubrication, such as medical grade silicone oil, can be used to lubricate the interactive components of valve assembly 20. Compressible seal 44, and more specifically interior surface 146 and raised annular rib 158, are also preferably coated with an oil. The oil prevents interior surface 146 and raised annular rib 158 from sticking together as shaft 210 is retracted from within compression chamber 88 to open first passageway 148 through compressible seal 44.

Rotatable end cap 46 is attached to proximal end 84 of housing 42. Shaft 210 is received within compression chamber 88 (FIG. 2) against slip ring 48. Correspondingly, proximal end 84 of housing 42 is disposed within recessed chamber 198 (FIG. 2) of rotational end cap 46. Second annular ridge 224 on distal end 212 of shaft 210 is received in second access 177 (FIG. 2) in slip ring 48. Second ring 174 of slip ring 48 encircles second annular ridge 224 and is disposed in fourth annular retaining groove 230 (FIG. 2) on distal end 212 of shaft 210.

Compression collar 118 on housing 42 has an outer diameter that is slightly larger than the inner diameter of compression ring 200 formed on interior surface 196 of sidewall 188 of end cap 46 to assist in retaining end cap 46 over housing 42. When end cap 46 is first attached over housing 42, compression ring 200 and distal end 184 of end cap 46 expands radially outward by the camming effect of compression collar 118 as compression ring 118 is passed through to recessed chamber 98 of end cap 46. Once compression collar 118 has passed beyond compression ring 200, distal end 184 of end cap 46 returns to its original configuration such that abutment of compression ring 200 against compression collar 118 assists in retaining proximal end 84 of housing 42 within recessed chamber 198 of rotatable end cap 46.

First engagement threads 120 of housing 42 are configured to complementary engage second engagement threads 202 of end cap 46 in rotational engagement. Fhe rotational engagement between first engagement threads 120 and second engagement threads 202 causes shaft 210 to advance within compression chamber 88 against either slip ring 48 or tubular compressible seal 44 depending on the embodiment of valve assembly 20.

First engagement threads 120 and second engagement threads 202 are one embodiment of structure capable of performing the function of a means for coupling shaft 210 to housing 42 and for selectively advancing shaft 210 into compression chamber 88 so as to compress compressible seal 44 within compression chamber 88. Various other embodiments of such a means for carrying out this function may be provided without detracting from the inventive nature of valve assembly 20.

The present invention also envisions using all other comparable configurations or alternative types of coupling and advancing. By way of example and not limitation, first engagement threads 120 could be positioned on interior surface 90 of compression chamber 88 while second engagement threads 202 would then be complementarily positioned on exterior surface 216 of shaft 210 for coupling and advancing shaft 210 within compression chamber 88. Alternatively, complimentary sets of barbs or ridges could replace first engagement threads 120 and second engagement threads 202. As shaft 210 is advanced within compression chamber 88, the complimentary sets of barbs or ridges can mechanically interact to couple shaft 210 to housing 42.

As illustrated in FIG. 3, lumen 50 in body 12, aperture 78 in cone-shaped membrane 40 of resilient seal 36, bore 86 in housing 42, first passageway 148 in compressible seal 44, and entryway 220 through shaft 210 are all in substantial axial alignment and in communication with each other.

Figure 4:
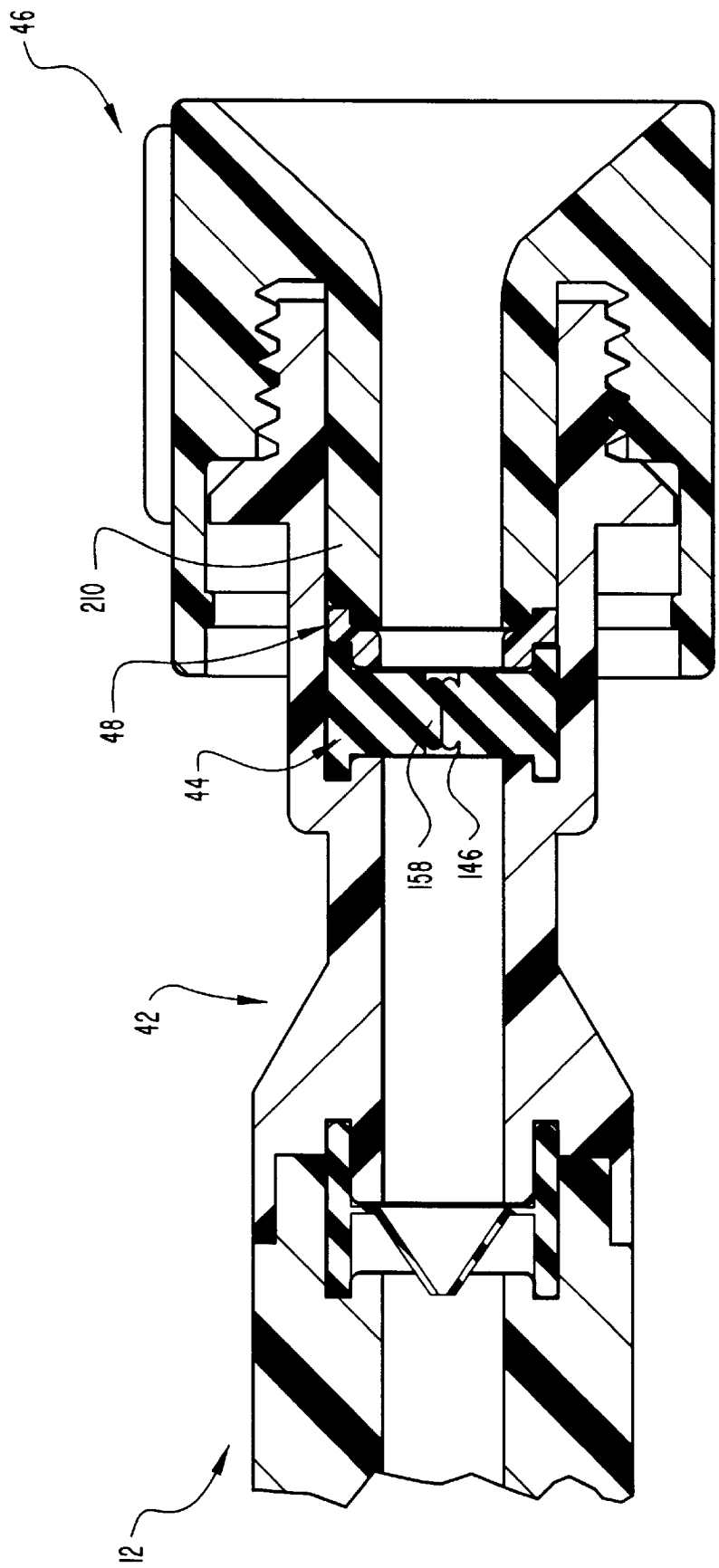
FIG. 4 is an enlarged cross-sectional view of the valve assembly of FIG. 3 in which the compressible seal is in a compressed and sealed position.

To constrict first passageway 148 within compressible seal 44, end cap 46 is rotated relative to housing 42, causing shaft 210 to advance within compression chamber 88 (see FIG. 2) as discussed above. As depicted in FIG. 4, as shaft 210 advances compressible seal 44 is compressed which causes raised annular rib 158 and interior surface 146 of compressible seal 44 to project radially inward, thereby tending to constrict first passageway 148 (FIG. 2) within compressible seal 44. Simultaneously, compressible seal 44 compresses radially outwardly against interior surface 90 of compression chamber 88 (FIG. 2) so as to form a seal therebetween. Shaft 210 can continue to be advanced until raised annular rib 158 is pressed together against itself to completely close and seal passageway 148 through compressible seal 44.

In use with a medical device, as depicted in FIG. 5, an elongated member 250 may be longitudinally disposed through passageway 148 of compressible seal 44 and aperture 78 of cone-shaped membrane 40 in resilient seal 36 for insertion into the cardiovascular system of a patient. FIG. 5 depicts adaptor 10 with elongated member 250 disposed therein prior to compressing compressible seal 44 thereagainst by rotating end cap 46 to advance shaft 210. With elongated instrument 250 disposed in resilient seal 36, cone-shaped resilient membrane 40 substantially forms a seal around elongated member 250. Cone-shaped membrane 40 is configured to substantially stop the loss of any fluids beyond interior recess 52 (FIG. 2) of body 12. It is possible, however, that in some instances some amount of body fluids that may pass through aperture 78 of membrane 40 into bore 86 of housing 42.

In light of this, compressible seal 44 is configured to prevent the passage of any fluids that may pass beyond membrane 40. Compressible seal 44 is designed to form a seal around elongated instrument 250 and for selectively opening and closing longitudinal bore 86 in housing 42 in response to a compressive force exerted thereon. Raised annular rib 158 is configured to allow elongated instrument 250 to be repositioned or removed while still maintaining a seal capable of substantially preventing the passage of body fluids beyond compressible seal 44 without having to release substantially all of the compressive forces acting on compressible seal 44.

When compressible seal 44 is in a completely uncompressed condition, as shown in FIG. 5, a slight gap 240 will generally exist between raised annular rib 158 and elongated instrument 250. However, gap 240 is sufficiently small such that even when compressible seal 44 is substantially uncompressed, raised annular rib 158 will be able to block the majority of fluids that may have passed beyond resilient seal 36 into bore 86.

Figure 6:
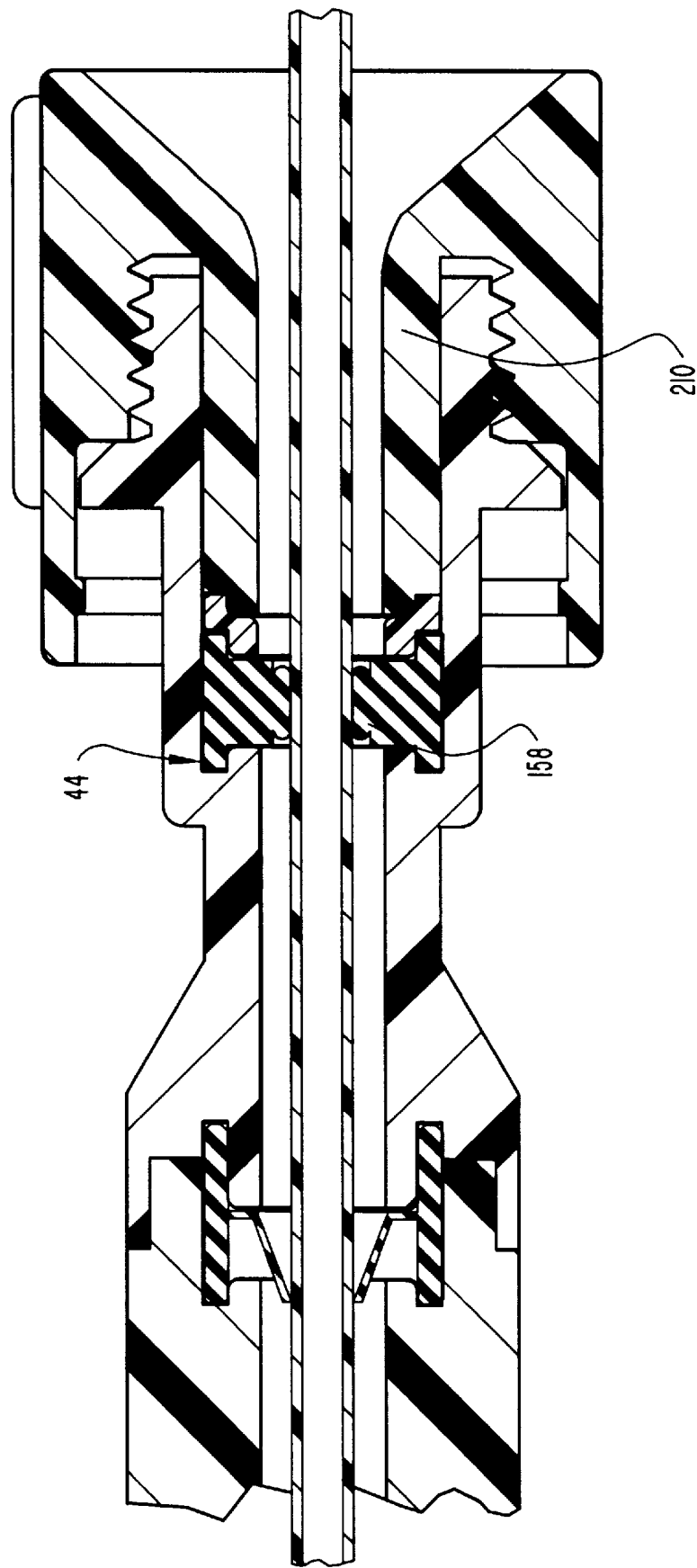
FIG. 6 is an enlarged cross-sectional view of the valve assembly of FIG. 5 showing the compressible seal in a compressed and sealed position.

In order to form a complete seal around instrument 250, end cap 46 may be rotated slightly to cause shaft 210 to exert a compressive force on slip ring 48, which in turn transfers the compressive force to compressible seal 44. As depicted in FIG. 6, the compressive force causes raised annular rib 158 and interior surface 146 of compressible seal 44 to move radially inward in an amount sufficient to close gap 240 and to form a seal about elongated instrument 250. In a preferred condition, raised annular rib 158 will exert very little radial force against elongated instrument 250 while nevertheless maintaining an adequate seal. This allows for longitudinal adjustments or removal of elongated instrument 250 to be made without the user having rotate end cap 46 to release all the compressive force acting on compressible seal 44 every time elongated instrument 250 is to be moved.

Raised annular rib 158 of compressible seal 44 is configured to incrementally adjust the tightness of the seal around elongated instrument 250 in precise increments when end cap 46 is rotated. The user of valve assembly 20 is able to selectively advance rotatable end cap 46 to precisely adjust the tightness of the seal formed around elongated instrument 250 as desired. The tightness of the seal around elongated instrument 250 is directly related to the amount of force exerted by raised annular rib 158 on elongated member 250. This provides a "sealing window" where compressible seal 44 remains sealed around elongated instrument 250 in varying amounts by exerting varying amounts of force on elongated instrument 250 while still allowing elongated instrument 250 to be repositioned or even removed.

Selectively advancing shaft 210 by rotating end cap 46 to cause compressible seal 44 to constrict in turn causes annular rib 158 and interior surface 146 to incrementally compress radially in order to gradually and progressively form a tighter seal around elongated instrument 250. Thus, as end cap 46 is selectively rotated to compress compressible seal 44, raised annular rib 158 exerts an increasing amount of radial force upon elongated instrument 250. In this way, selectively rotating end cap 46 incrementally controls the tightness of the seal formed by raised annular rib 158 around elongated member 250.

Moreover, compressible seal 44 is configured such that when it is compressed causing raised annular rib 158 to bulge radially inward and to contact elongated instrument 250, a seal is quickly formed although only a minor compressive force may be applied initially. Continued advancement of end cap 46 increases the compressive force acting on compressible seal 44 and, consequently, the force acting on elongated instrument 250 by raised annular rib 158. The amount of compressive forces acting on the elongated instrument 250 may be selectively controlled by rotating end cap 46 and is often referred to in industry as the "drag" acting on elongated instrument 250. Advantageously, the user of adaptor 10 can minimize the drag acting on elongated instrument 250 if desired when repositioning or moving elongated instruments 250 while still maintaining an adequate seal about elongated instrument 250. As such, elongated member 250 can be repositioned or even removed while maintaining a seal sufficient to substantially minimize the loss of body fluid from valve assembly 20.

FIGS. 7–10 illustrate alternate embodiments of adaptor 10. The majority of features previously discussed apply to the alternative embodiments and will tend to function in substantially similar manner. The features that remain substantially unchanged are identified with the same reference numbers as used in FIGS. 1–6. Only those features that have been substantially altered will be renumbered and described in detail.

Figure 7:
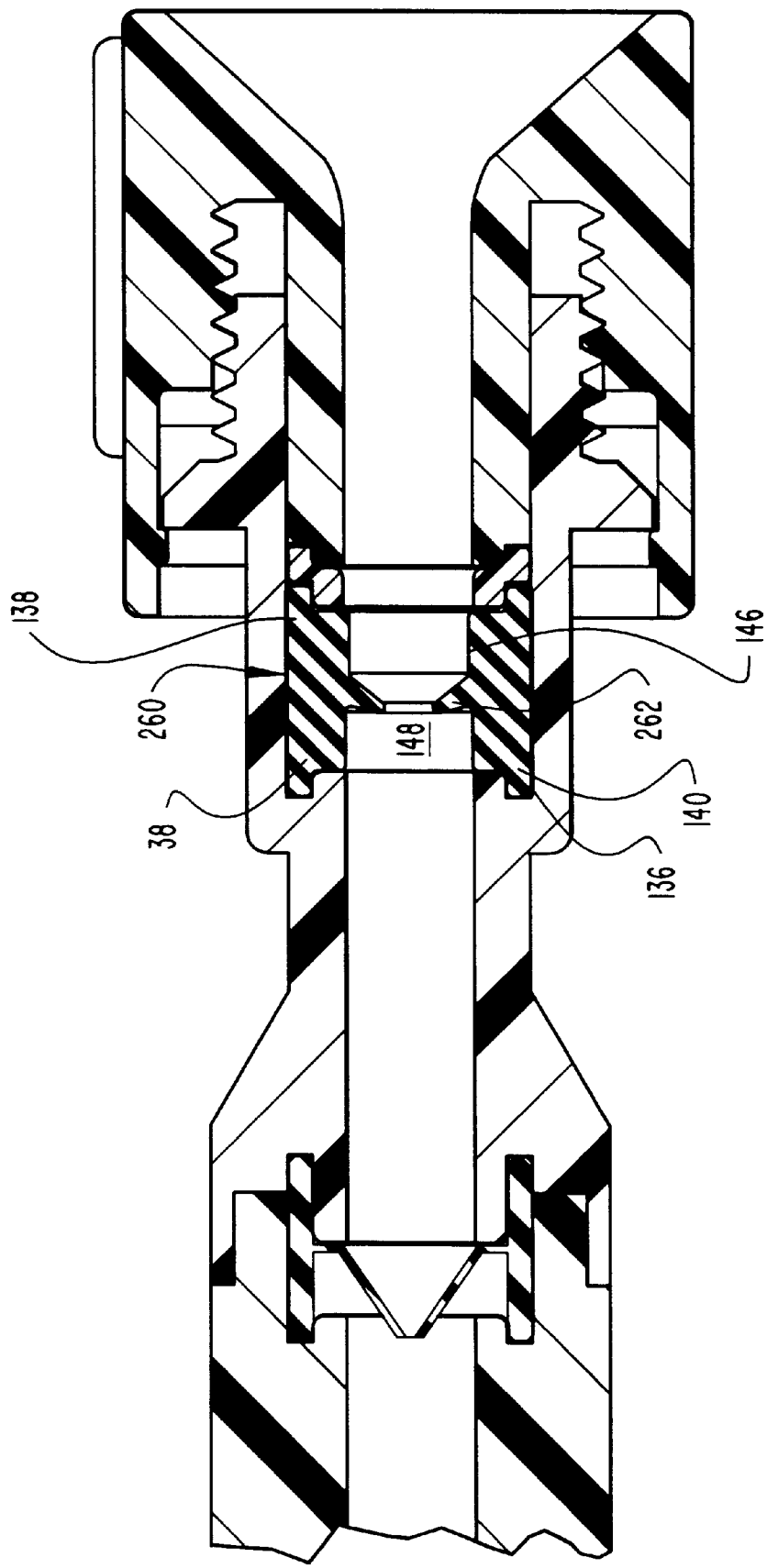
FIG. 7 is an enlarged cross-sectional view of the valve assembly of FIG. 3 with an alternate embodiment of the compressible seal.

FIG. 7 illustrates an alternative embodiment of valve assembly 268 employing an alternate compressible seal 260 in place of compressible seal 44. Alternate compressible seal 260 comprises a generally elongated cylindrical body portion 38 that has an exterior surface 136 and an interior surface 146 extending between a proximal end 138 and a distal end 140. Alternate compressible seal 260 also comprises a raised annular portion such as, by way of example and not by limitation, an annular fin 262 that is integrally formed on interior surface 146 and extends into first passageway 148. Alternate compressible seal 260 is compressed in the same manner as compressible seal 44 illustrated in FIGS. 1–6 causing annular fin 262 and interior surface 146 to move radially inward to form a seal in response to the compressive force exerted by rotating end cap 46.

Figure 8:
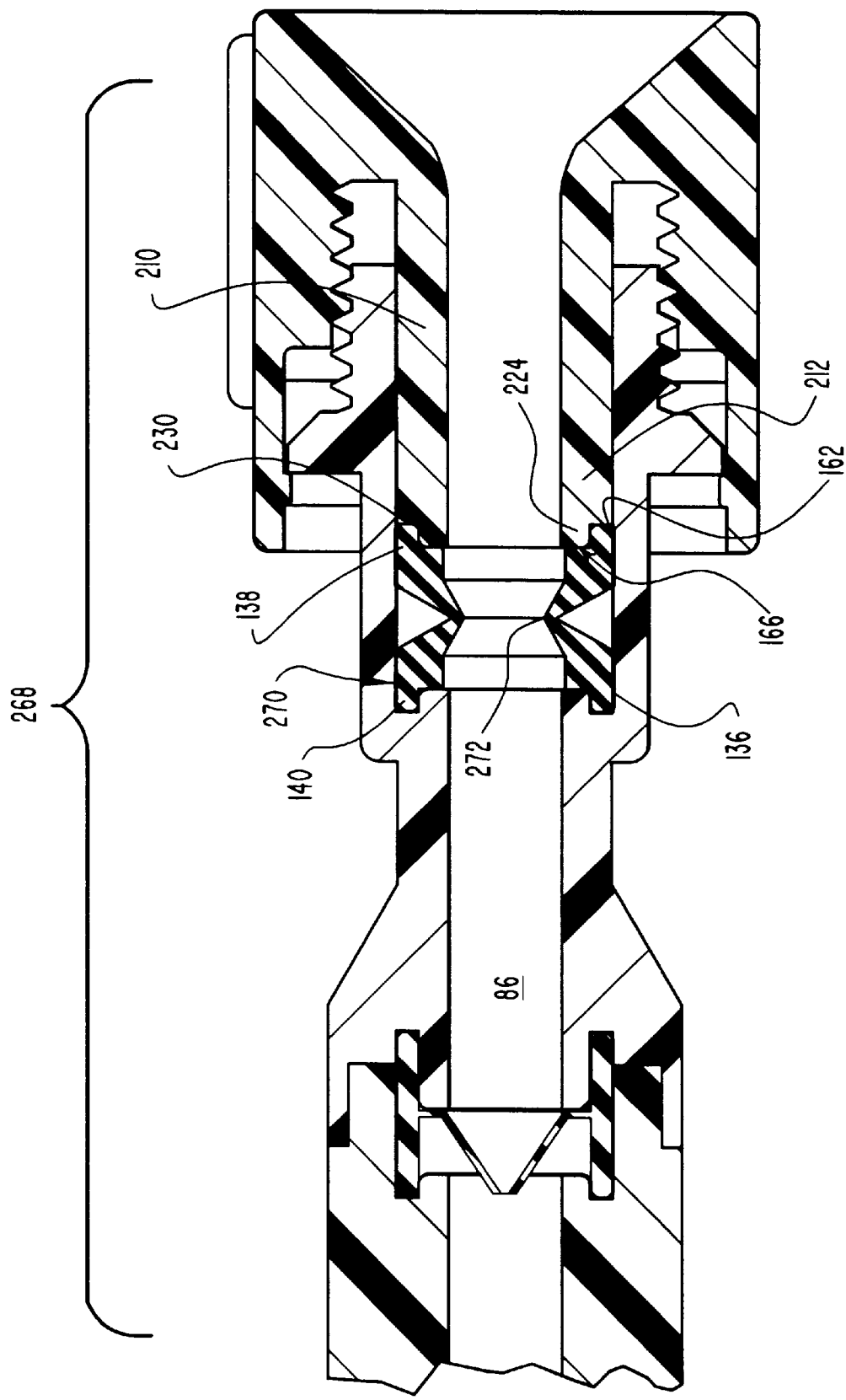
FIG. 8 is an enlarged cross-sectional view of the valve assembly of FIG. 3 with another alternative embodiment of the compressible seal.

FIG. 8 illustrates an alternative valve assembly 268 having another alternate compressible seal 270 but which does not include the optional slip ring 48 depicted in FIGS. 1–7. Alternate compressible seal 270 has an exterior surface 136 and an interior surface 146 extending between a proximal end 138 and a distal end 140. Interior surface 146 has a substantially hour-glass-shape and defines a first passageway 148 that extends longitudinally through alternate compressible seal 270 and is axially aligned with bore 86. The hour-glass shape of interior surface 146 of alternate compressible seal 270 creates a raised annular portion such as, by way of example and not limitation, central peak 272 at the narrowest portion of alternate compressible seal 270 in first passageway 148. Exterior surface 136 as illustrated is substantially hour-glass shaped. It could, however, be substantially cylindrical.

Because valve assembly 268 does not include optional slip ring 48, shaft 210 of rotatable end cap 46 cooperates directly with proximal end 138 of alternate compressible seal 270. Specifically, second annular ridge 224 on distal end 212 of shaft 210 is disposed within second recess 166 (FIG. 2) in proximal end 138 of alternate compressible seal 270. Simultaneously, annular second tongue 160 that projects proximally from proximal end 138 of compressible seal 270 is disposed in fourth annular retaining groove 230 (FIG. 2). Proximal end face 162 of second tongue 160 contacts distal end 212 of shaft 210. When compressive force is exerted upon compressible seal 270, center peak 272 moves radially inward to form a seal either against itself or about elongated instrument 250 when elongated instrument 250 is inserted through first passageway 148.

Figure 9:
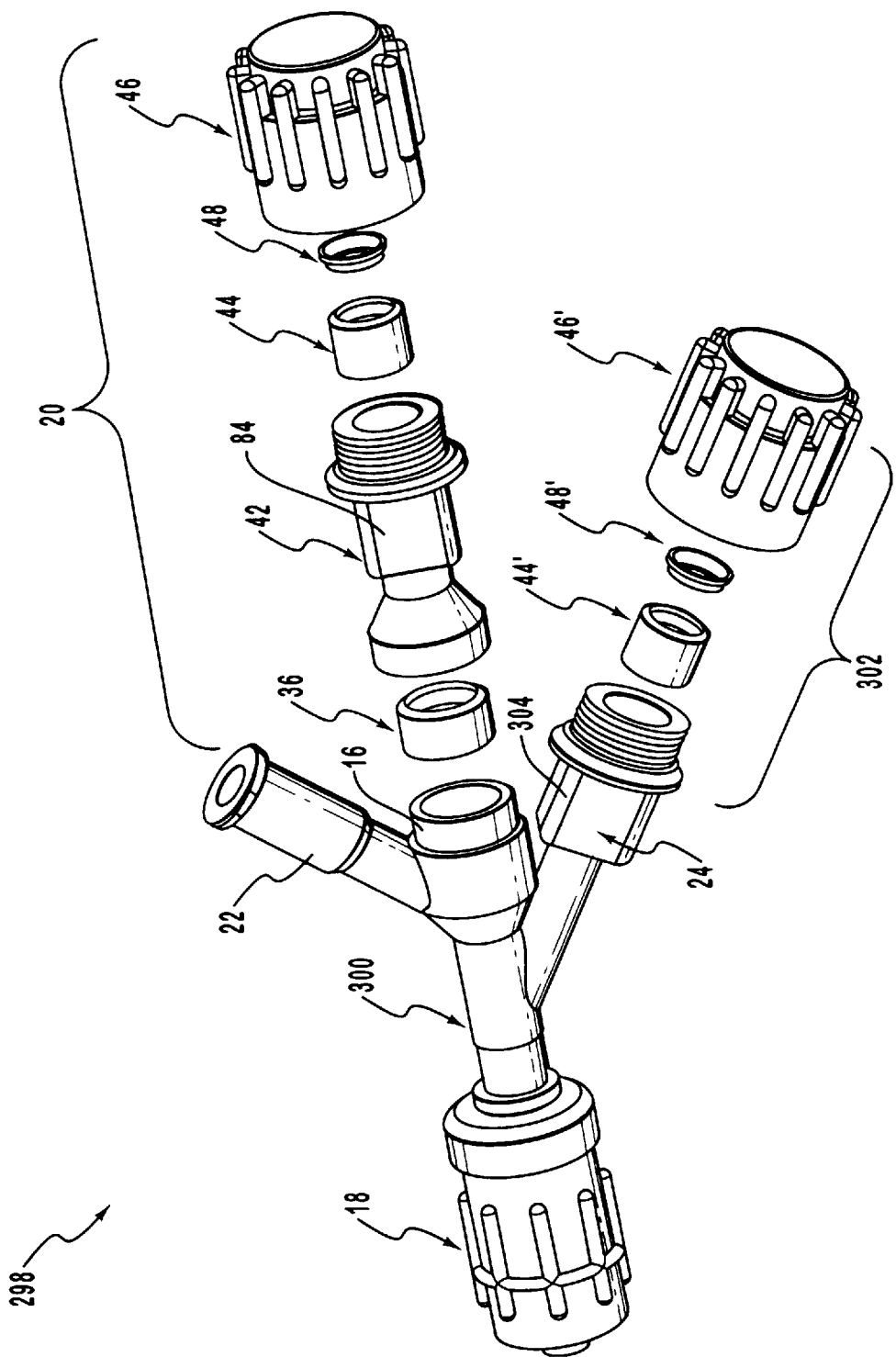
FIG. 9 is an enlarged prospective view of an alternate embodiment of the adaptor of FIG. 1 having a peripheral valve assembly in a partially disassembled condition.

FIG. 9 illustrates an alternate embodiment of an adapter 298. Adaptor 298 includes a tubular body 300 that comprises first supplemental access tube 22 and second supplemental access tube 24, and valve assembly 20, which was depicted in FIGS. 1–8 and previously discussed. First supplemental access tube 22 and second supplemental access tube 24 each have a central bore formed therethrough so as to be in fluid communication with tubular body 300. First and second supplemental access tubes 22 and 24, respectively, are, configured to be placed in fluid communication with an elongated instrument such as a catheter; can be used for introducing fluids or other medical devices into the body of a patient; and are each preferably positioned at an angle relative to the longitudinal axis of tubular body 300 so as to project outwardly towards proximal end 16 of tubular body 300. It can be appreciated that adaptor 298 and tubular body 300 may have other configurations that may be equally effective in carrying out the intended function thereof.

Second supplemental access tube 24 includes a peripheral valve assembly 302 that is similar to a portion of valve assembly 20. Peripheral valve assembly 302 includes a housing 304, a compressible seal 44', a rotatable end cap 46', and an optional slip ring 48'. Housing 304 is substantially the same as the proximal end 84 of housing 42 shown in FIGS. 1 and 2. Compressible seal 44', optional slip ring 48', and rotatable end cap 46' are preferably similar to those various embodiments shown and discussed relative to FIGS. 1–8.

Figure 10:
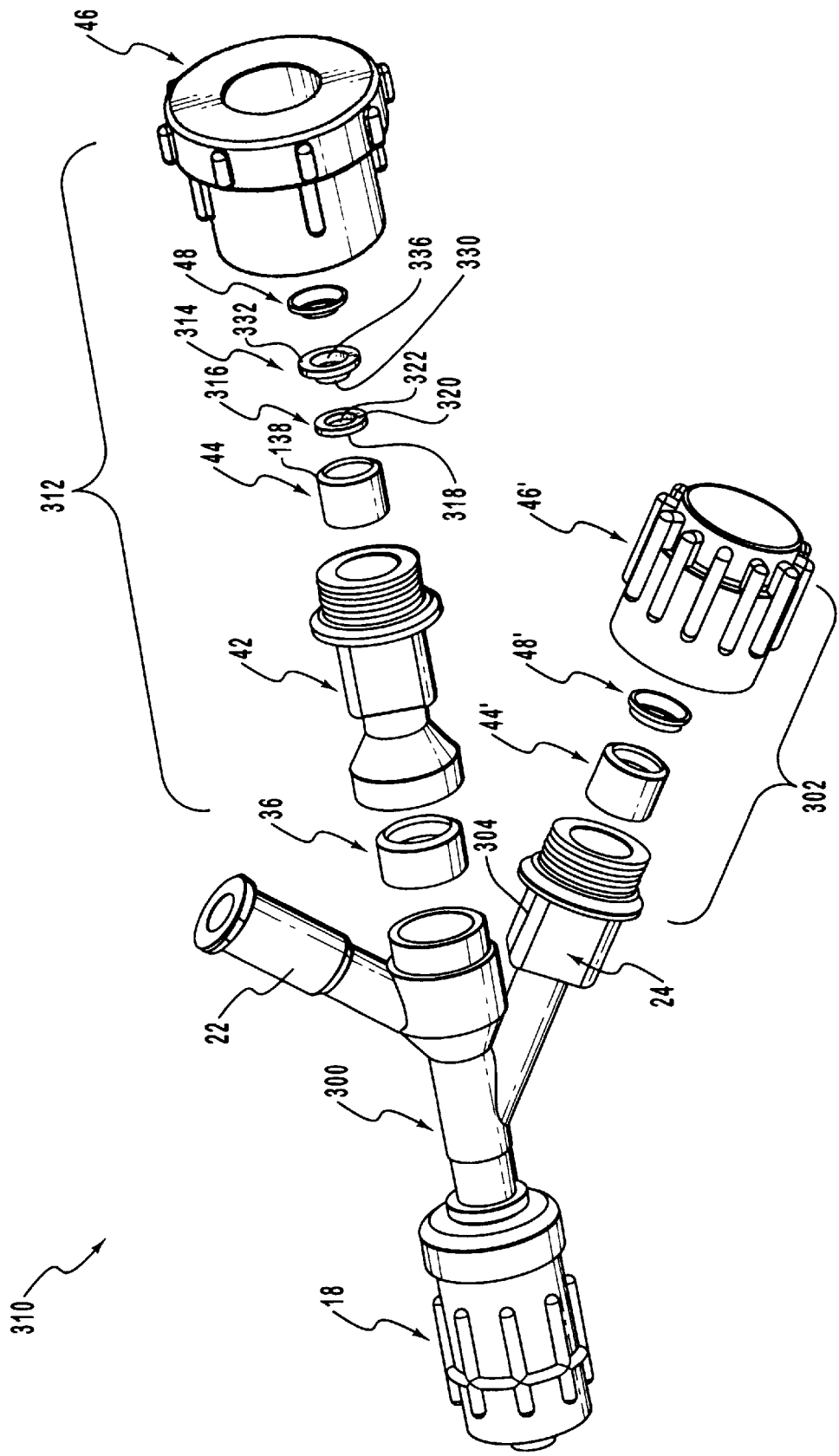
FIG. 10 is an enlarged prospective view of the adaptor of FIG. 9 with an alternate embodiment of the valve assembly.

FIG. 10 illustrates an alternate embodiment of adaptor 298 depicted in FIG. 9. Adaptor 310 depicted in FIG. 10, however, includes an alternative valve assembly 312 in place of valve assembly 20. Like valve assembly 20, alternative valve assembly 312 comprises a resilient seal 36, a housing 42, a compressible seal 44, and a slip ring 48, as were previously discussed in various forms relative to FIGS. 1–9. In addition to the features previously discussed or any alternate embodiments thereof, valve assembly 312 comprises a second compressible seal 3 14 and a washer 316. Compressible seal 44 is configured to cooperate with washer 316 and second compressible seal 314. In addition, second recess 166 in proximal end 138 (FIG. 2) of compressible seal 44 may be elongated or deepened longitudinally to better receive and accommodate both of washer 316 and second compressible seal 314 therein as discussed more fully below.

Washer 316 has a distal face 318 and a proximal face 320 and is configured to cooperate with second recess 166 in proximal end 138 of compressible seal 44. The outside diameter of washer 316 is substantially the same as the diameter of second recess 166 in proximal end 138 of seal 44. The inside diameter of washer 316 defines an opening 322 that is axially aligned with first passageway 148 (FIG. 2) in compressible seal 44.

Valve assembly 312 also comprises resiliently deformable second compressible seal 314. Second compressible seal 314 is configured to cooperate with compressible seal 44, washer 316, and slip ring 48 or shaft 210 of end cap 46, depending on whether or not the embodiment includes the optional slip ring 48. Second compressible seal 314 includes a main portion 330 and a shoulder portion 332. The outer diameter of main portion 330 is substantially equal to the diameter of second recess 166 (FIG. 2) in compressible seal 44 so that the distal end of main portion 330 of second compressible seal 314 can be received within of compressible seal 44. In this embodiment, second recess 166 (FIG. 2) should have sufficient longitudinal depth to receive washer 316 and main portion of second compressible seal 314 therein. Washer 316 is disposed between second compressible seal 314 and compressible seal 44.

As depicted in FIG. 10, both main portion 330 and shoulder portion 332 of second compressible seal 314 are substantially cylindrical in shape. It can be appreciated that main portion 330 of second compressible seal 314 may have other configurations as long as second compressible seal 314 and second recess 166 (FIG. 2) in proximal end 138 of compressible seal 44 are configured to cooperate.

Shoulder portion 332 is configured to cooperate with both compression chamber 88 (FIG. 2) of housing 42 and first ring 170 (FIG. 2) of slip ring 48 or shaft 210 (FIG. 2), depending on the embodiment. The outside diameter of shoulder portion 332 of second compressible seal 314 is substantially equal to the inner diameter of compression chamber 88, thereby allowing compressible seal 44, washer 316, second compressible seal 314, and optional slip ring 48 to all be disposed within compression chamber 88. The inner diameter of shoulder portion 332 is substantially the same as the outside diameter of first ring 170 (FIG. 2) of slip ring 48 and is configured to receive first ring 170 therein. If slip ring 48 is not used, the inner diameter of shoulder portion 332 should be substantially equal to the outside diameter of annular second ridge 224 on distal end 212 of shaft 210 (FIG. 2).

The inner diameter of shoulder portion 332 of second compressible seal 314 forms a third recess 336 capable of retaining first ring 170 therein. Main portion 330 has an interior surface that defines a passageway (not shown) that extends longitudinally therethrough and is axially aligned with opening 322 in washer 316 and passageway 148 (FIG. 2) in compressible seal 44. The passageway of main portion 330 of second compressible seal 314 has a diameter smaller than the diameter of third recess 336 formed in shoulder portion 332. A support surface (not shown) extends from the diameter of third recess 336 to the passageway (not shown). It can be appreciated that various other configurations of shoulder portion 332, compression chamber 88, and slip ring 48 may be utilized that are equally effective in carrying out the intended function thereof.

Like compressible seal 44, second compressible seal 314 has a raised annular portion (not shown) integrally formed on the interior surface of the passageway. The raised annular portion (not shown) of second compressible seal 314 may have any appropriate configuration as previously discussed, including raised annular rib 158 of compressible seal 44, raised annular fin 262 of compressible seal 260, or central peak 272 of compressible seal 270. In this embodiment, the raised annular portion (not shown) of second compressible seal 314 may be the same as or differ from the corresponding feature found within the compressible seal 44. When valve assembly 312 is assembled, compressible seal 44, washer 316, and second compressible seal 314 will adjacently reside within housing 42.

In the embodiment shown in FIG. 10 it is preferable that compressible seal 44 and second compressible seal 314 comprise different elastomeric materials or silicon rubber having different durometer readings. In particular, it is preferred that compressible seal 44 comprise a material that is harder than the material comprising second compressible seal 314. As a result of the different hardnesses of materials, when a compressive force is exerted upon both compressible seal 44 and second compressible seal 314, they will compress radially inward at different rates and, consequently, will form seals at different times.

For example, if second compressible seal 314 comprises a material that is softer than the material comprising compressible seal 44, second compressible seal 314 will form a seal prior to compressible seal 44. In addition, second compressible seal 314 will compress radially inward further than compressible seal 44 and thereby exert a greater sealing force on elongated instrument 250 when the same force is applied to both compressible seal 44 and second compressible 314. Second compressible seal 314 is one example of structure capable of performing the function of a third sealing means for progressively opening and closing longitudinal bore 86 and housing 42 in combination with second sealing means.

In all the embodiments of adapters of the present invention, tubular bodies 12 and 300, housing 42, and rotatable end piece 46 preferably comprise a clear, transparent polycarbonate plastic. Such a plastic material allows for relatively easy molding, moderate flexibility, and the ability to see the internal components and operation of the adapters. Of course, alternative types of conventional plastics can also be used depending on one's taste and the intended use of a particular adaptor.

Valve assembly 20, or alternate embodiments thereof, can be used for various functions. In one position, valve assembly 20 can be used to completely block off proximal end 16 of tubular body 12 so as to prevent the escape of blood or other bodily fluids flowing from a patient into adaptor 10. Alternatively, valve assembly 20 can be used to form a seal around a medical instrument such as elongated instrument 250 when the instrument is received within valve assembly 20 past tubular body 18 and into the cardiovascular system of a patient. Valve assembly 20 also prevents the back flow of bodily fluids from leaking out of adaptor 10 when an elongated member is removed from valve assembly 20. Valve assembly 20 is also configured to allow a user to selectively adjust the amount of compression acting upon compressible seal 44 by means of rotatable end cap 46. The amount of compression acting on compressible seal 44 directly affects the amount of drag acting on elongated instrument 250 and felt by the medical practitioner. By selectively adjusting the amount of compression acting on compressible seal 44, valve assembly 10 is capable of forming an adequate seal around elongated instrument 250 while minimizing the drag in order to allow elongated instrument 250 to be repositioned or removed without having to rotate end cap 46 each time.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A valve apparatus comprising:
   (a) body means for providing a lumen therethrough and which is adapted for accessing the cardiovascular or other intravenous system of a patient;
   (b) housing means, attached to said body means, for providing a longitudinal bore therethrough in communication with said lumen, said housing means including a compression chamber;
   (c) resilient first sealing means, disposed in said body means, for substantially blocking and controlling the loss of body fluids from said lumen, said first sealing means comprising a body portion having an interior surface and a cone-shaped membrane portion attached to said interior surface of said body portion;
   (d) resiliently deformable second sealing means, disposed within said compression chamber, for selectively sealing and unsealing said longitudinal bore in response to a compressive force exerted on said second sealing means, said second sealing means including a longitudinal passageway therethrough which communicates with said longitudinal bore and provides an opening thereto, said second sealing means assuming a normally open position when not subjected to said compressive force, said second sealing means responding to said compressive force so as to selectively and progressively reduce the size of said opening; and
   (e) compressing means attached to said housing means for selectively increasing and decreasing said compressive force on said second sealing means.

2. A valve apparatus recited in claim 1, when said compressing means is rotatable such that said compressive force can be increased when said compressing means is rotated in one direction relative to said housing means and such that said compressive force can be decreased when said compressing means is rotated in an opposite direction relative to said housing means.

3. A valve apparatus as recited in claim 2, further comprising second holding means for interlocking a proximal end of said second sealing means such that when said rotatable compressing means is rotated relative to said body means said proximal end of said second sealing means is substantially prevented from rotating.

4. A valve apparatus as recited in claim 3, wherein said second holding means comprises:
   (f) a ridge projecting from a proximal end of said compressing means and defining a retaining groove positioned between said ridge and an outer perimeter of said compression chamber; and
   (g) a tongue proximally projecting from said proximal end of said second sealing means and received within said retaining groove.

5. A valve apparatus as recited in claim 2, further comprising slip ring means, disposed between said second sealing means and said rotatable compressing means, for reducing rotational biasing between said compressing means and said second sealing means upon rotating said compressing means relative to said second sealing means.

6. A valve apparatus as recited in claim 5, wherein said slip ring means comprises a slip ring positioned between said second seal means and said compressing means, said slip ring comprising:
   (a) a first ring portion configured to be received within a corresponding recess at a proximal end of said second sealing means; and
   (b) a second ring portion secured proximal to said first ring portion and configured to cooperate with said compressing means.

7. A valve apparatus as recited in claim 2, wherein said rotatable compressing means comprises a shaft and means for engaging said shaft and said second sealing means by selectively advancing said shaft into said compression chamber, and said coupling means comprising:
   (a) first engagement threads positioned at a proximal end of said housing means; and
   (b) second engagement threads positioned at a distal end of said rotatable compressing means, said second engagement threads being configured for threadably engaging said first engagement threads once said shaft is partially received within said compression chamber.

8. A valve apparatus recited in claim 1, wherein said first sealing means comprises a membrane portion with an aperture formed therein.

9. A valve apparatus as recited in claim 1, wherein said membrane portion comprises a material selected from the group consisting of silicon rubber and elastomer materials.

10. A valve apparatus as recited in claim 1, wherein said second sealing means comprises a compressible seal having an interior surface defining said longitudinal passageway and having a raised annular portion protecting into said longitudinal passageway.

11. A valve apparatus as recited in claim 10, wherein said compressible seal has an outer surface that is substantially cylindrical-shaped so as to correspond to a substantially cylindrical-shaped compression chamber.

12. A valve apparatus as recited in claim 10, wherein said raised annular portion of said compressible seal comprises an annular rib.

13. A valve apparatus as recited in claim 10, wherein said raised annular portion of said compressible seal comprises a fin.

14. A valve apparatus as recited in claim 10, wherein said compressible seal has a substantially hour-glass shaped configuration when in a substantially uncompressed state.

15. A valve apparatus as recited in claim 10, wherein said interior surface of said compressible seal is substantially hour-glass shaped, wherein said raised annular portion comprises a raised central peak located at a narrowest point of said longitudinal passageway formed by said hour-glass shaped interior surface.

16. A valve apparatus as recited in claim 1 further comprising holding means for interlocking a distal end of said second sealing means within said housing means such that when said compressive force is exerted on said second sealing means the distal end of said second sealing means is prevented from entering said longitudinal bore of said housing means.

17. A valve apparatus as recited in claim 16, wherein said holding means comprises:
   (a) a ridge projecting into said compression chamber toward a proximal end of said housing means, said ridge defining a retaining groove positioned between said ridge and an outer perimeter of said compression chamber; and
   (b) a tongue distally projecting from said distal end of said sealing means and received within said retaining groove.

18. A valve apparatus as recited in claim 17, wherein said ridge is annular and encircles said longitudinal bore so that said retaining groove is annular, wherein said tongue is annular so that it correspondingly mates with said retaining groove.

19. A valve apparatus comprising:
   (a) body means for providing a lumen therethrough and which is adapted for accessing the cardiovascular or other intravenous system of a patent, said body means including an interior recess;
   (b) housing means, attached to said body means, for providing a longitudinal bore therethrough in communication with said lumen, said housing means comprising a hollow compression chamber;
   (c) resilient sealing means, at least a portion of which is disposed within said recess of said body means, for substantially blocking and controlling the loss of body fluids from said lumen, said sealing means comprising a generally cone-shaped membrane portion having an apex and an aperture formed through said apex;
   (d) a resiliently deformable compressible seal disposed within said compression chamber for selectively sealing and unsealing said longitudinal bore in response to a compressive force exerted on said compressible seal, said compressible seal having a longitudinal passageway therethrough which communicates with said longitudinal bore of said housing means and provides an opening thereto, said longitudinal passageway of said compressible seal having a raised annular portion formed therein, said elongated compressible seal assuming, a normally open position when not subjected to said compressive force, said compressible seal responding to said compressive forces so as to selectively and progressively reduce the size of said opening provided by said passageway; and
   (e) compressing means, rotatably attached to said housing means, for selectively increasing said compressive force on said compressible seal when said compressing means is rotated in one direction relative to said housing means and for selectively decreasing said compressive force on said seal when said compressing means is rotated in an opposite direction relative to said housing means, said compressing means comprising an elongated shaft means for contacting a proximal and of said compressible seal so as to exert said compressive force on said compressible seal, wherein said raised annular portion formed in said passageway of said compressible seal is configured to allow an instrument accessing said lumen to be repositioned or removed while maintaining a seal capable of preventing substantially all loss of body fluids beyond said compressible seal without rotating said compressing means to release substantially all of said compressive force acting on said compressible seal.

20. A valve apparatus as recited in claim 19, further comprising slip ring means, disposed between said compressible seal and said compressing means, for reducing rotational biasing between said compressing means and said compressible seal upon rotating said compressing means relative to said compressible seal.

21. A valve apparatus as recited in claim 19, wherein said raised annular portion of said compressible seal comprises an annular rib.

22. A valve apparatus as recited in claim 19, further comprising a compressible sealing means, disposed adjacent said compressible seal, for selectively sealing and unsealing said longitudinal bore in said housing means in combination with said compressible seal, said compressible sealing means and said compressible seal comprising varying materials, respectively, having different durometer readings, thereby causing said compressible sealing means and said compressible seal to form a seal at varying rates in response to application of said compressive force.

23. A valve apparatus as recited in claim 22, wherein said compressible sealing means comprises a second compressible seal having a second longitudinal passageway formed therethrough and a raised annular portion that projects into said second longitudinal passageway.

24. A valve apparatus comprising:
   (a) a generally elongated tubular body having a lumen formed therethrough which is adapted for accessing the cardiovascular or other intravenous system of a patient, said tubular body including an interior recess in communication with said lumen and located adjacent a proximal end of said tubular body;
   (b) an elongated housing attached to said proximal end of said tubular body and including a longitudinal bore formed therethrough, said housing having an interior hollow compression chamber formed in the proximal end thereof and in communication with said longitudinal bore;
   (c) a resilient seal including a resilient cone-shaped membrane portion capable of substantially blocking the loss of body fluids from said lumen, said membrane portion having an aperture formed at an apex thereof;
   (d) a resilient compressible seal substantially disposed within said compression chamber and including a longitudinal passageway formed therethrough aligned and in communication with said longitudinal bore and a raised annular ridge projecting into said passageway, said raised annular ridge selectively providing an opening to said longitudinal bore, said compressible seal assuming a normally open position when not subjected to said compressive force, said compressible seal being configured to selectively seal and unseal said bore in response to a compressive force exerted on said compressible seal by selectively and progressively reducing and increasing the size of said opening provided by said annular ridge, said annular ridge being capable of forming a seal around an instrument disposed therein sufficient to substantially prevent any body fluids that may pass through said aperture of said cone-shaped membrane portion from passing through said longitudinal passageway while being adjustable to allow for longitudinal movement and adjustment of said instrument; and (e) a rotatable end cap attached to said housing and having a shaft integrally formed therewith, said shaft projecting from said end cap and being configured to partially fit within said compression chamber of said housing in order to selectively compress said compressible seal when said shaft is advanced within said compression chamber by rotation of said end cap.

25. A valve apparatus as recited in claim 24, further comprising a second compressible seal disposed between said compressible seal and said shaft of said rotatable end cap, said second compressible seal having a second longitudinal passageway formed therethrough in communication with said longitudinal passageway of said compressible seal said compressible seal and said second compressible seal having different hardnesses such that each responds to said compressive force at differing rates.

26. A valve apparatus as recited in claim 24 further comprising:

(a) a supplemental access tube having a central bore formed therethrough in fluid communication with said lumen in said tubular body, said supplemental access tube including a compression chamber formed in a remote end thereof and being in communication with said central bore;

(b) a resilient deformable auxiliary sealing means, substantially disposed within said compression chamber of said supplemental access tube for selectively sealing and unsealing said central bore in response to an auxiliary compressive force exerted on said auxiliary sealing means, said auxiliary sealing means including a longitudinal passageway therethrough which communicates with said central bore in said supplemental access tube and which provides an opening thereto, said auxiliary sealing means assuming a normally open position when not subjected to said auxiliary compressive force, said sealing means responding to said auxiliary compressive force so as to selectively and progressively reduce the size of said opening provided by said central bore; and (c) auxiliary compressing means, rotatably attached to a remote end of said supplemental access tube, for selectively increasing said auxiliary compressive force on said auxiliary sealing means when said auxiliary compressing means is rotated in one direction relative to said supplemental access tube, and for selectively decreasing said auxiliary compressive force on said auxiliary sealing means when said auxiliary compressing means is rotated in an opposite direction relative to said supplemental access tube.

* * * * *

UNITED STATES PATENT AND TRADEMARK OFFICE
CERTIFICATE OF CORRECTION

PATENT NO.   : 5,935,112
DATED        : August 10, 1999
INVENTOR(S)  : Brian W. Stevens, Arlin Dale Nelson It is certified that error appears in the above-identified patent and that said Letters Patent is hereby corrected as shown below:

Column 3,
Line 58, after "guidewire" and before "be" insert -- to --

Column 7,
Line 29, before "shown" change "arc" to -- are --

Column 8,
Line 14, after "inner" change "surface103" to -- surface 103 --
Line 60, after "collar" change "1118" to -- 118" --

Column 13,
Line 39, after "ring" change "118" to -- 200 --
Line 49, after "engagement." change "Fhe" to -- The --

Column 15,
Line 13, after "having" and before "rotate" insert -- to --
Line 26, after "remains" change "scaled" to --sealed --

Column 17,
Line 17, after "seal" change "3 14" to -- 314 --

Column 18,
Line 52, after "ible" and before "314" insert -- seal --

Column 19,
Line 13, after "cap 46." change "I he" to -- The --

UNITED STATES PATENT AND TRADEMARK OFFICE
CERTIFICATE OF CORRECTION

PATENT NO.    : 5,935,112
DATED         : August 10, 1999
INVENTOR(S)   : Brian W. Stevens, Arlin Dale Nelson It is certified that error appears in the above-identified patent and that said Letters Patent is hereby corrected as shown below:

Column 20,
Line 56, after "portion" change "protecting" to -- projecting --

Column 21,
Line 12, after "second" change "scaling" to -- sealing --
Line 35, after "system of a " change "patent" to -- patient --

Column 22,
Line 4, after "proximal" change "and" to --end --

Signed and Sealed this

Ninth Day of October, 2001

*Attest:*

*Attesting Officer*

NICHOLAS P. GODICI
*Acting Director of the United States Patent and Trademark Office*